United States Patent
Park et al.

(10) Patent No.: US 9,339,365 B2
(45) Date of Patent: May 17, 2016

(54) DEVICE AND METHOD FOR DELIVERING GRAFTS

(76) Inventors: David D. Park, Duluth, GA (US); Rebecca Copenhaver Delegge, Mt. Pleasant, SC (US); Ashley Hancock, Atlanta, GA (US)

(*) Notice: Subject to any disclaimer, the term of this patent is extended or adjusted under 35 U.S.C. 154(b) by 954 days.

(21) Appl. No.: 13/363,460

(22) Filed: Feb. 1, 2012

(65) Prior Publication Data

US 2013/0012966 A1 Jan. 10, 2013

Related U.S. Application Data

(60) Provisional application No. 61/550,600, filed on Oct. 24, 2011, provisional application No. 61/563,321, filed on Nov. 23, 2011, provisional application No. 61/573,587, filed on Sep. 8, 2011, provisional application No. 61/571,857, filed on Jul. 7, 2011.

(51) Int. Cl.
  *A61F 2/00* (2006.01)
  *A61B 17/34* (2006.01)
  *A61B 17/00* (2006.01)

(52) U.S. Cl.
  CPC ........... *A61F 2/0063* (2013.01); *A61B 17/3421* (2013.01); *A61B 17/00234* (2013.01); *A61B 17/3468* (2013.01); *A61B 2017/00597* (2013.01); *A61B 2017/00623* (2013.01); *A61B 2017/00991* (2013.01); *A61B 2017/3433* (2013.01); *A61B 2017/3486* (2013.01); *A61F 2002/0072* (2013.01)

(58) Field of Classification Search
  CPC .................... A61B 17/0057; A61B 17/00234; A61F 2/0063; A61F 2002/0072
  USPC .......................... 623/1.23, 1.25; 606/151, 213
  See application file for complete search history.

(56) References Cited

U.S. PATENT DOCUMENTS

| | | | |
|---|---|---|---|
| 5,147,316 A * | 9/1992 | Castillenti | ................ 604/164.04 |
| 5,379,754 A | 1/1995 | Tovey et al. | |
| 5,405,360 A | 4/1995 | Tovey | |
| 5,957,939 A | 9/1999 | Heaven et al. | |
| 6,425,924 B1 | 7/2002 | Rousseau | |
| 6,478,803 B1 | 11/2002 | Kapec et al. | |
| 6,669,735 B1 | 12/2003 | Pelissier | |
| 7,662,112 B2 * | 2/2010 | Zamierowski et al. | ....... 600/587 |
| 7,947,054 B2 | 5/2011 | Eldar et al. | |
| 7,963,992 B2 | 6/2011 | Cauthen, III et al. | |
| 8,641,699 B2 | 2/2014 | Hansen | |
| 2007/0185506 A1 | 8/2007 | Jackson | |
| 2008/0195121 A1 | 8/2008 | Eldar et al. | |
| 2009/0254103 A1 | 10/2009 | Deutsch | |

(Continued)

*Primary Examiner* — Julian W Woo
*Assistant Examiner* — Michael Mendoza
(74) *Attorney, Agent, or Firm* — B. Craig Killough; Barnwell Whaley Patterson & Helms

(57) ABSTRACT

A device and method for delivering a graft or synthetic mesh for anatomical repair to the repair site, with the graft or synthetic mesh in position for attachment to repair the defect. A plurality of spaced apart, flexible fingers is connected to the graft or synthetic mesh. The flexible fingers are initially in a position that is generally parallel to a direction of travel of the actuator. The actuator moves the plurality of flexible fingers from the initial to form a radial array, which opens or extends the graft or synthetic mesh. The graft or synthetic mesh may then be attached. A novel trocar is disclosed that is useful with the device. A measuring device including a measuring scale that is useful for determining the required size of the graft is also disclosed.

28 Claims, 16 Drawing Sheets

(56) References Cited

U.S. PATENT DOCUMENTS

| | | |
|---|---|---|
| 2010/0069930 A1 | 3/2010 | Roslin et al. |
| 2010/0069947 A1 | 3/2010 | Sholev et al. |
| 2010/0130850 A1* | 5/2010 | Pakter .......................... 600/411 |
| 2010/0179576 A1 | 7/2010 | Halevy |
| 2012/0016409 A1 | 1/2012 | Sherwinter et al. |

* cited by examiner

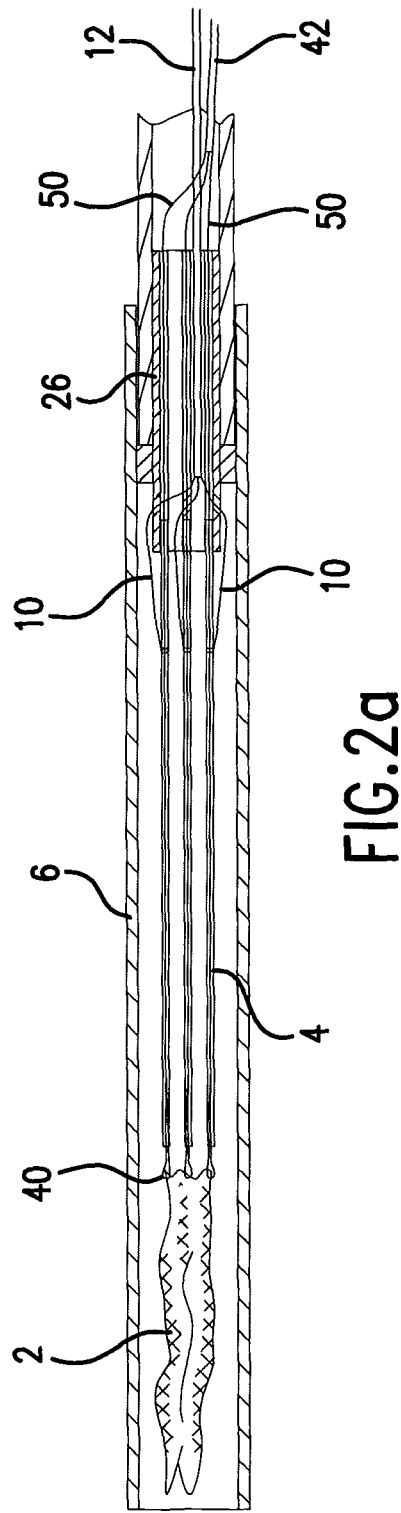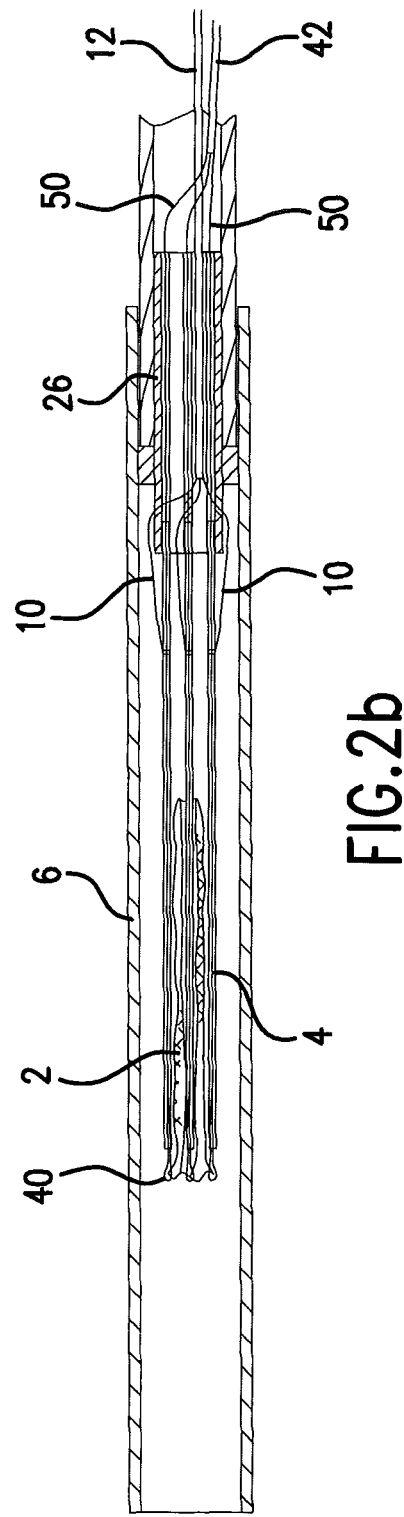

DEVICE AND METHOD FOR DELIVERING GRAFTS

Applicant claims the benefit of U.S. Provisional Application Ser. Nos. 61/573,587 filed Sep. 8, 2011; 61/571,857, filed Jul. 7, 2011; 61/550,600, filed Oct. 24, 2011 and 61/563,321, filed Nov. 23, 2011.

FIELD OF THE INVENTION

This invention relates to medical devices and methods generally, and is more specifically related to a device and method of delivering a graft for attachment to tissue.

BACKGROUND OF THE INVENTION

Biological grafts and synthetic mesh are used to repair anatomical defects, such as hernias. Delivery of the mesh or graft into body cavities either requires invasive surgery, or heretofore unsatisfactory laparoscopic methods.

Hernias are structural defects most commonly involving the musculofascial tissues of the abdominal and pelvic regions within the human body. Some hernias involve internal muscular defects (i.e., diaphragmatic, hiatal hernias) while most involve the abdominal wall. Common types of abdominal wall hernias include inguinal, femoral, umbilical, ventral and incisional hernias. Unless they are completely without associated symptoms, most hernias eventually require surgical repair. Some of the common hernia symptoms include activity-induced pain, uncomfortable visible bulges, alteration in bowel function, and incarcerated or strangulated internal organs within the hernia resulting in emergent surgical intervention.

It is estimated that approximately 800,000 to 900,000 hernia operations are performed annually in the United States of which 200,000 involve ventral variety. Ventral hernias may be primary hernias (i.e., epigastric, Spiegelian hernias) but most commonly are incisional types which sometimes form after surgical incisions are made through the abdominal wall for the purpose of gaining access into the internal organs for various operations.

Surgical repair of ventral incisional hernias may be accomplished via an "open method." This method involves making a sizable incision directly over the tissue defect, separating the contents of the hernia away from the musculofascial defect, and repairing the defect primarily using sutures, or more commonly, sewing a graft to the defect edge in tension-free manner. This is done in an effort to minimize the recurrence of hernia formation which, unfortunately, occurs with some frequency. The recurrence may be due to multiple factors including general health of the patient, surgical technique, and types of mesh or graft utilized. Overall, this traditional method is effective, but also often involves more pain, longer periods of disability following the surgery, higher perioperative infection rates, and an established hernia recurrence rate.

Alternatively, ventral incisional hernias may be repaired using the "laparoscopic method." This method utilizes endoscopic or laparoscopic approach in which multiple tiny incisions are made remote from the musculofascial defect, trocars placed through these small incisions for access to the internal abdomen, internal organs or tissues separated from the hernia defect, a mesh or graft delivered through the trocar in some fashion, mesh or graft positioned over the defect and finally, graft or mesh secured around the defect with sutures and/or various fixation devices. This method is advantageous over the "open method" due to lesser surgical pain, shorter period of disability following surgery, lower infection rate and perhaps lower hernia recurrence rate. However, these perceived benefits are subject to vigorous debate within the surgical community.

Currently, approximately 30 to 40 percent of ventral incisional hernias are repaired using the laparoscopic method. However, this method has its own set of major shortcomings principally related to higher degree of difficulty in performing this procedure. One of the major challenges involve graft introduction into the abdominal cavity. Typically, a graft is rolled tightly into a cylindrical configuration and subsequently, pushed/pulled through the trocar which can be both time consuming and frustrating, especially when a larger graft is needed to cover the defect. This maneuver can also damage the graft during the delivery due to excessive force used or needed during the delivery process. Some surgeons also elect to place multiple sutures within the periphery of the graft for transfascial securement. This is often done prior to introduction of the graft. Once delivered into the abdominal cavity, the rolled graft/suture combination is unrolled, sutures isolated into respective corresponding abdominal quadrants, and the graft is centered over the defect prior to fixation. These steps are often very challenging and frustrating to accomplish in an efficient manner due to the pliable property of the graft and sutures which is a desired characteristic.

In addition, due to the change in concavity of the inner abdominal wall within versus the outer skin surface, correct sizing of the mesh or graft is compromised. This situation leads to an overestimation of the needed mesh or graft size, leading to further difficulties. These shortcomings contribute to a reason that laparoscopic methods, despite advantages, are less commonly utilized by many surgeons at the present time.

There is a need for a device and method that overcomes the deficiencies of current endoscopic or laparoscopic procedures, such as those used for ventral hernia repair. This new surgical device allows precise yet effortless delivery of a larger prosthetic mesh or graft via a novel trocar design for subsequent graft fixation. It also allows for more precise sizing of the defect thus eliminating a major frustration often encountered when working with a large piece of mesh or graft.

SUMMARY OF THE INVENTION

The present invention is a device and method for delivering a synthetic mesh or graft for anatomical repair at the defect site, with the synthetic mesh or graft in position for attachment to repair the defect. A plurality of spaced apart, flexible fingers is connected to the synthetic mesh or graft. The flexible fingers are initially in a position that is generally parallel to a direction of travel of the actuator. The actuator moves the plurality of flexible fingers from the initial position to form a radial array, which opens or extends the synthetic mesh or graft. The synthetic mesh or graft may then be secured in place.

A novel trocar is disclosed that is useful with the device. The length of the trocar is variable. Components for retaining the trocar in position for use with the delivery device are provided. A measuring device including a measuring scale that is useful for determining the required size of the graft is also disclosed.

DESCRIPTION OF THE DRAWINGS

FIG. 2a is a partial, sectioned view of the device for delivery of a graft for attachment to tissue as shown in FIG. 1.

FIG. 2b is a partial, sectioned view of another embodiment of the device for delivery of a graft for attachment to tissue as shown in FIG. 1.

FIG. 14b is an exploded view of the novel trocar of FIG. 14a.

DETAILED DESCRIPTION OF PREFERRED EMBODIMENTS

Figure 1:
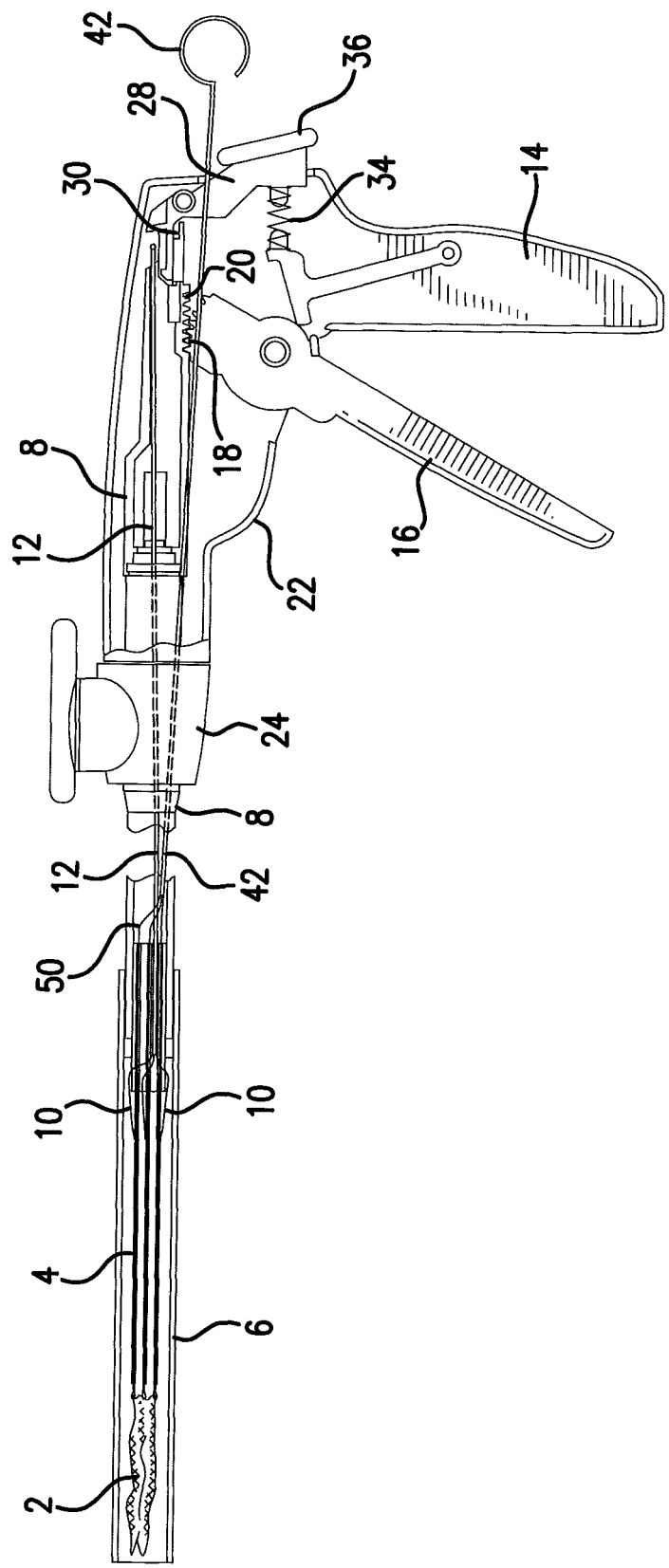
FIG. 1 is a sectioned view of an embodiment of a device for delivery of a graft for attachment to tissue.

Turning now to the drawing figures, FIG. 1 shows an embodiment of a delivery device for delivery of a graft or synthetic mesh 2 for attachment to tissue. The term "graft" is used herein to indicate either a graft formed of biological material, or a synthetic mesh. The graft is connected to a plurality of flexible fingers 4. The flexible fingers and graft, when positioned as shown in FIG. 1, may be present within a sheath 6. The flexible fingers are generally parallel to a central axis of the sheath, and generally parallel to an axis of travel of an actuator 8. Since the fingers are flexible, some bending of the fingers means that they may not be strictly parallel, but are generally parallel, to the axis of travel of the actuator while held in the position shown in FIG. 1 or FIG. 2.

Figure 3:
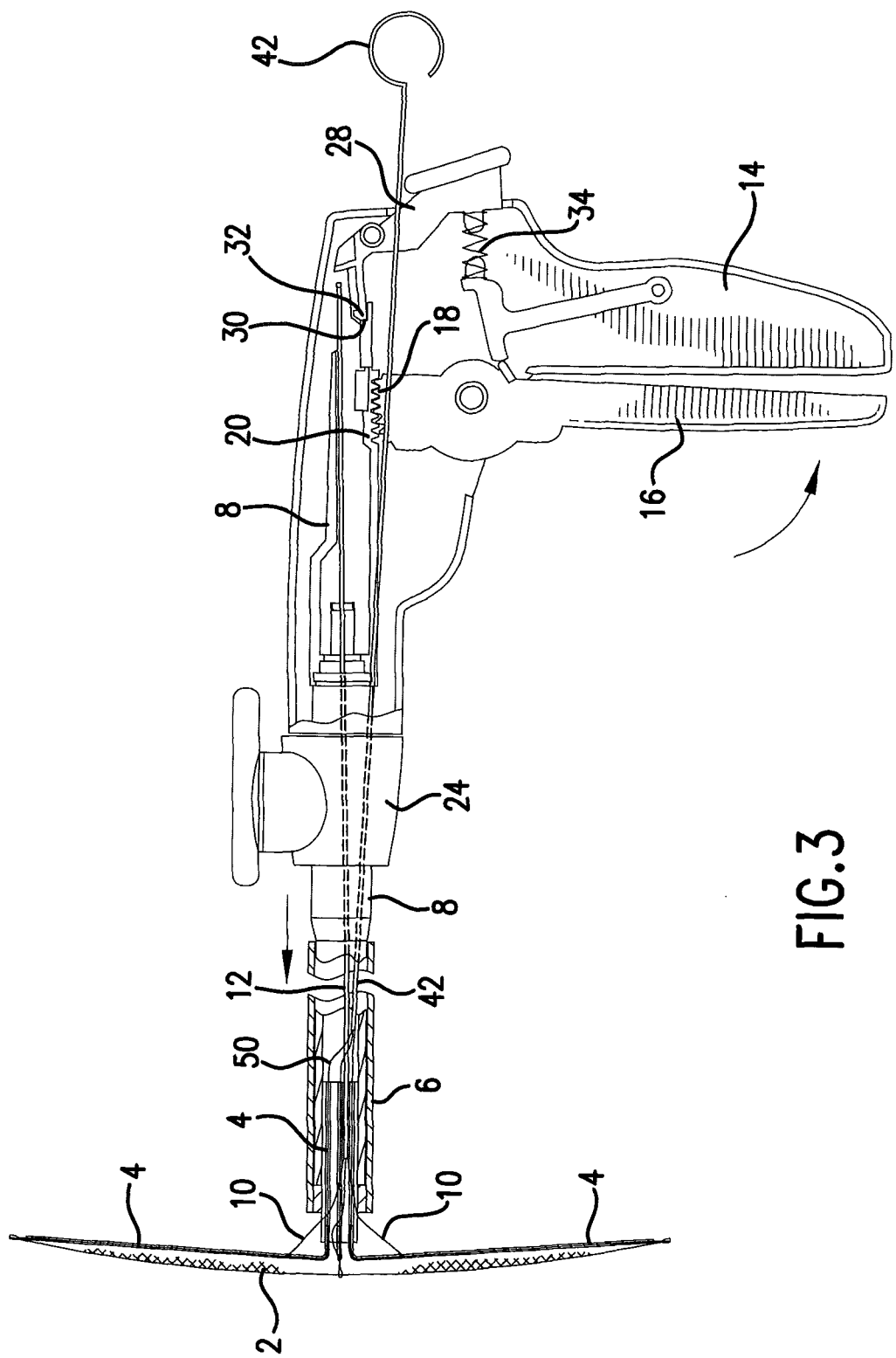
FIG. 3 is a sectioned view of the device for delivery of synthetic a graft to tissue as shown in FIG. 1, with the graft in an extended or open position.

FIG. 1 and FIG. 2 show the device for delivery of graft for attachment to tissue, according to an embodiment, prior to deployment of the graft. FIG. 3 shows the same embodiment of the device with the graft deployed. In this embodiment, the actuator pushes the flexible fingers outwardly. The flexible fingers of this embodiment are attached to, and move with, the actuator. The actuator moves outwardly away from the handle as demonstrated in FIG. 3, causing the flexible fingers to also move outwardly and away from the handle.

A plurality of control wires 10 may be attached to the handle, or to some stationary article associated with the handle (such as rod 12), at an end of the control wires that is proximal to the handle. The control wires are fixed to a point on the device so that they do not move as the actuator and flexible fingers move, so that the control wires will pull against the flexible fingers as the flexible fingers move outwardly and away from the handle. The control wires are connected to the flexible fingers at or near a distal end of the control wires. In a preferred embodiment, each of the plurality of control wires is associated with one of the plurality of the flexible fingers. Since the control wires are fixed at the proximal end and attached at the distal end to a point on the flexible fingers, while the flexible fingers are movable with the actuator, the control wires pull against the flexible fingers at the point of attachment as the flexible fingers move outwardly. The control wires are preferred to be nitinol wires, but the control wires could be formed of other metals, or plastics, textile materials or polymers, or similar materials having sufficient strength and flexibility.

Figure 4:
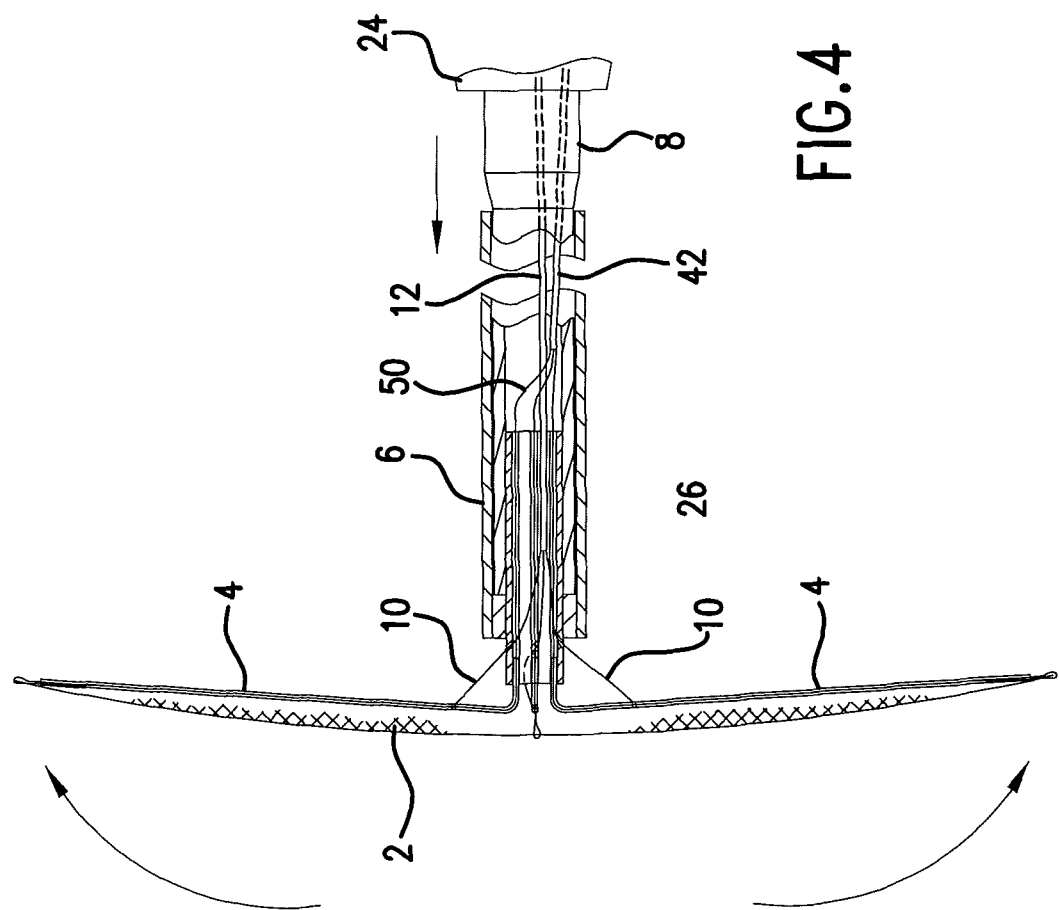
FIG. 4 is a partial, sectioned view of the device for delivery of a graft for attachment to tissue as shown in FIG. 3.

The control wires are fixed to the flexible fingers at a point that will provide the required arcuate travel of the flexible fingers as the device is actuated. This point of attachment may be spaced apart from the point of bending of the flexible fingers, and may be less than 25% of distance along the length of flexible fingers, as measured from the joinder of the flexible fingers to the holder and/or actuator to the distal end of the flexible fingers. FIG. 4. As shown, the control wires form a 30° to 60° degree angle relative to the flexible fingers when the actuator is fully advanced.

As used herein, "proximal" is closest to the operator of the device, and "distal" will typically be away from the operator, and toward the patient when the device is in use.

Figure 9:
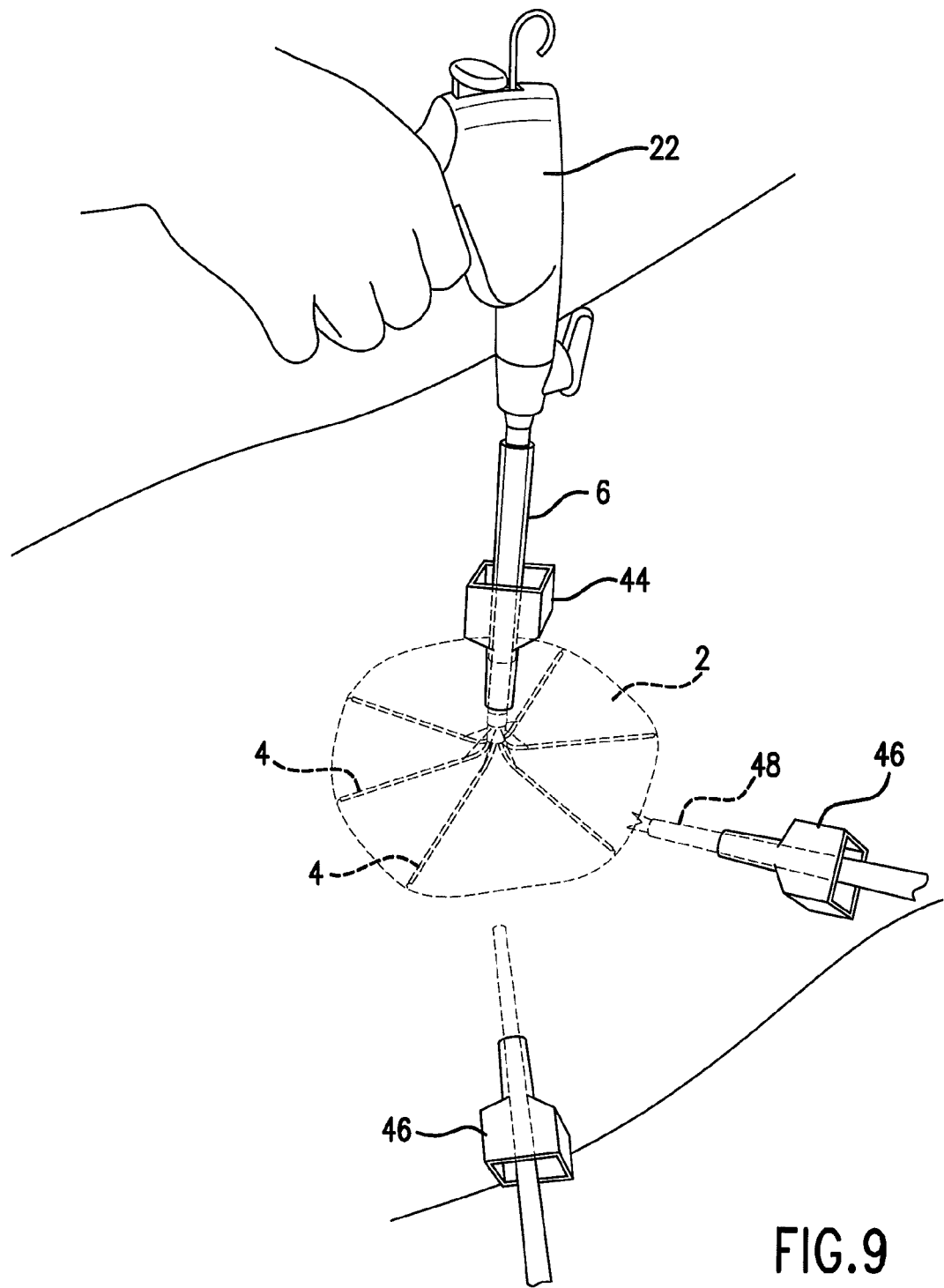
FIG. 9 demonstrates the graft for attachment to tissue as deployed by an embodiment of the device.

As demonstrated by FIG. 4, as the actuator moves outwardly and away from the handle, it pushes the flexible fingers outwardly. The control wires, being fixed, pull against the flexible fingers, moving the flexible fingers to a downward position as shown in FIG. 3 and FIG. 4. As the flexible fingers move downward, they form a radial array (FIG. 9) and unfold the graft to a generally planar position. In a preferred embodiment, the flexible fingers, as they are moved by the actuator and pulled down by the control wires, move past a position that is perpendicular to the axis of travel of the actuator, as shown in FIG. 3 and FIG. 4. In a preferred embodiment, when the travel of the actuator is fully exhausted and the actuator is in its most outward and distal position relative to the handle, the flexible fingers will be positioned at an angle of more than 90° from the axis of travel of the actuator, or the central axis of the sheath. In some embodiments, this angle could be up to 120°. The actuator may be designed to allow the operator to set the desired angle. In some embodiments then, the angle may be at least 100° and perhaps more, so that the edges, or periphery, of the graft are pulled against the defect of the patient for subsequent securing or suturing of the graft as shown in FIG. 9.

According to one embodiment of the invention as shown in FIG. 1 to FIG. 4, the device may comprise a pistol grip handle 14 having a trigger 16. The handle may form housing for the mechanism, including the actuator. The trigger pivots relative to the handle, and the trigger may comprise a gear 18 at the top of the trigger. The gear of the trigger engages a gear, such as a rack 20, which causes the actuator 8 to be advanced outwardly or retracted inwardly, and the movement may be linear. In this embodiment, the actuator slidably engages the housing 22 which forms the handle, and projects from the muzzle 24 of the handle, as can be seen when comparing the position of the trigger and actuator relative to the handle and muzzle in FIG. 1 with the position of the trigger and actuator relative to the handle and muzzle in FIG. 3.

At the distal end of the actuator, and preferably, externally to the muzzle of the housing, is the plurality of spaced-apart flexible fingers. These fingers may be attached to a holder 26. The holder may in turn be attached to the actuator, so that the flexible fingers are advanced and retracted by the actuator as it moves. The fingers may be mounted within the holder so as to be rotatable relative to the holder. Rotating the fingers relative to the actuator allows the spacing of the fingers to be modified if desired or necessary.

The flexible fingers are preferred to be formed of a flexible cable. The cable may be a hollow cable formed of coiled or spirally-wound material which is capable of repetitive flexing and bending. The cable may comprise stainless steel. This property of flexing and bending is necessary so that the cables can move outwardly relative to the handle and out of the sheath as shown in FIG. 1 and FIG. 2, and extend downwardly to the position shown in FIG. 3 and FIG. 4. Since the cables are subsequently retracted into the sheath by reversing the travel of the actuator by movement of the trigger from the position shown in FIG. 3 to the position shown in FIG. 1, the cables must also be sufficiently flexible to "snake" back into the sheath after detachment from the graft without disturbing the graft that is secured to tissue. The cables are preferred to be fully flexible along their length, without having preformed bends or angles that may tend to dictate a path of travel as the flexible fingers are withdrawn from the surgical site. The flexible cables used with the control wires allow the cables to follow the anatomical structure or host tissue as a path of travel as the cables are pulled away from the graft and toward the handle. Rigid members, rather than flexible cables, will resist removal, due to the anatomical structure or host tissue interfering with the path of travel.

In one embodiment, the flexible fingers are attenuated or weakened at intervals. This allows the operator to break of portions of the flexible fingers to more precisely match the length of the fingers with the size of the graft that is selected. The intervals may be spaced, for example, 1 cm apart, so that the length of the fingers may be reduced in 1 cm steps. In another embodiment, the length of the flexible fingers is varied by extending or retracting the flexible fingers relative to the device.

Movement of the flexible fingers from the position generally shown in FIG. 2 to the position shown in FIG. 4, which requires a movement through an arc, demonstrated by FIG. 4. This movement is accomplished by the resistive force applied to the cables by the control wires. The position of the control wires relative to the handle and the flexible fingers is fixed. That is to say, the control wires are attached at the proximal end to the handle, and not to the moving actuator. As the flexible cables move from the position of FIG. 1 to the position of FIG. 3, there is sufficient slack in the control wires to allow outward movement of the flexible fingers from the sheath, but only to a limiting point. The length of the control wires is such that as the flexible fingers move outwardly, the control wire attached to its associated flexible finger at a fixed point becomes taught, and exerts force on the flexible finger, pulling the flexible finger back toward the handle. In this embodiment, when travel of the actuator, and the flexible fingers, is exhausted, the flexible fingers, and the graft attached thereto, is in the position shown in FIG. 4. As further demonstrated by FIG. 9, the flexible fingers, form a radial array. There may be as few as four (4) flexible fingers, and as many as eight (8) flexible fingers, depending on the size of the graft, and according to preference of the user.

According to a preferred embodiment of the invention, a locking mechanism is provided that holds the trigger in the position shown in FIG. 3 when the graft is deployed as shown in FIG. 3 and FIG. 4. As shown in the drawing figures, the end of the actuator, or a device that is a slidable communication with the actuator, engages a spring biased and pivoting member 28 that engages and holds the trigger and actuator, relative to the handle and muzzle, in a locked position. In this embodiment, a notch 30 at the end of the actuator causes the locking mechanism to rotate due to spring biasing 34, engaging the locking lug 32 with the notch, and preventing the trigger from rotating from the position shown in FIG. 3. Once the graft is positioned, it is not necessary for the surgeon or other operator to hold the trigger to keep the graft in the position shown in FIG. 4 or FIG. 9 while suturing the graft. The thumb control 36 allows the locking lug to be rotated in the opposite position and away from the notch, to again allow the trigger to be moved back to the position of FIG. 1. This movement causes the actuator to be pulled within the muzzle of the housing, returning the flexible fingers to the position shown in FIG. 2.

At or near a distal end of the flexible fingers, a connector 40 is provided for connecting the graft to each of the flexible fingers. This connection may be controlled by control rod 42.

Figure 5:
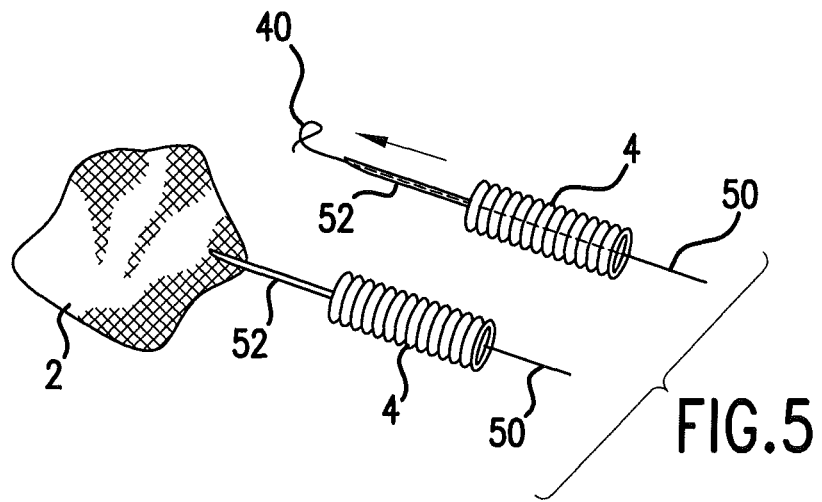
FIG. 5, FIG. 6 and FIG. 7 show progressive attachment of a graft for attachment to tissue according to an embodiment of the device.
Figure 6:
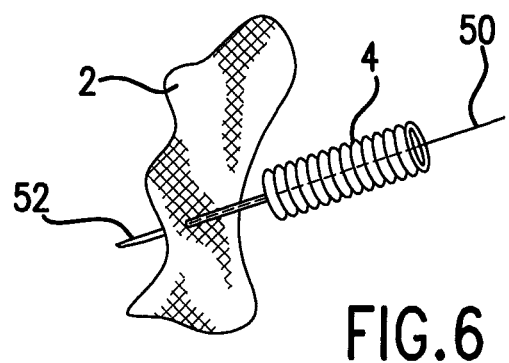
Figure 7:
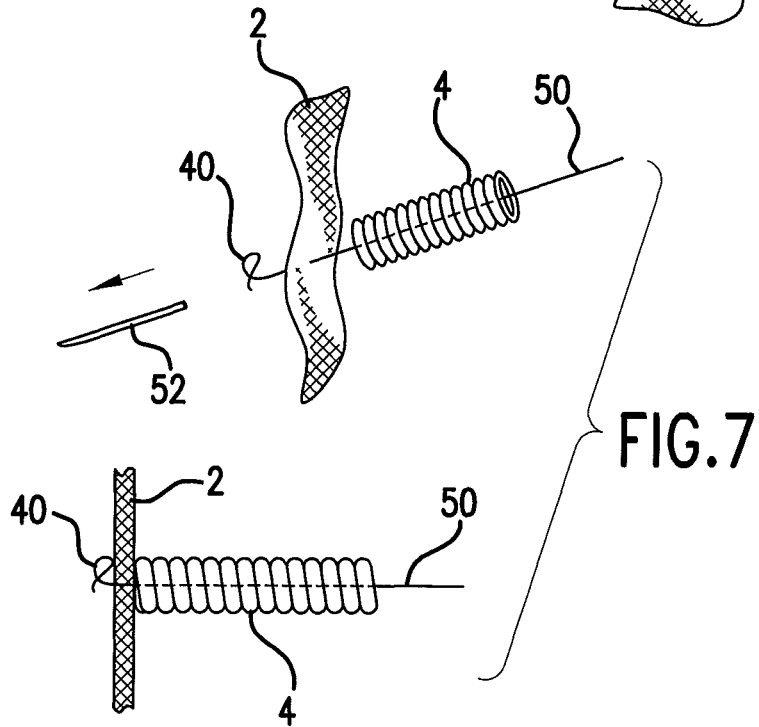

In the embodiment shown in FIG. 5, FIG. 6 and FIG. 7, the connector is formed in a wire. The connector may be formed in a portion of a connector wire 50, such as a distal end of the wire, coiled to form a pigtail. The connector wire may be nitinol wire than has the pigtail shape imparted as shape memory, but is sufficiently deformable with low levels of force applied so as to allow the connector wire to be connected and disconnected from the graft. One connector wire is preferred to be associated with each flexible finger. The connector wire is present in a lumen of the hollow cable from which the flexible fingers are formed in a preferred embodiment, and the wire may be manipulated within the lumen. The plurality of connector wires are in turn connected at a proximal end to a control rod 42.

A preferred method of attaching the graft to the flexible fingers is described. The device is preferably in the position shown in FIG. 3. A needle 52 may be attached over the end of the connector wire as shown in FIG. 5. The needle may be slotted for attachment to the wire. The needle is used to straighten the pigtail. The needle is pushed through the graft, delivering the pigtail to the opposite, distal, side of the graft. FIG. 6. The needle is then pushed from the end of the connector wire, allowing the pigtail connector to remain on the distal side of the graft. FIG. 7. The graft is connected to the flexible arms by abutting the pigtail connector on one side and the flexible arm on the other. This process is repeated for each of the flexible arms.

To remove the pigtail connectors, the control rod 42 is used to pull the connectors through the graft to the operator or proximal side of the graft. Disconnection of the flexible fingers from the graft will typically occur after the graft is sutured in place, and the device is in the position shown in FIG. 9. The control rod pulls the pigtail connector through the graft. The pigtail connector is sufficiently deformable to be straightened enough by the pulling action through the graft so as to disconnect from the graft.

After attachment of the graft, the actuator is positioned fully toward the handle, so that the device is in the position shown in FIG. 1. The sheath 6 aids in folding the graft. The graft may be folded within the interior of the plurality of flexible fingers (FIG. 2b) or outside of the flexible fingers (FIG. 2a), and the sheath protects the graft in normal handling, and as the device is inserted through a port, such as trocar 44. The sheath may be a sleeve that is slidable to be advanced away from the handle, or retracted toward the handle, to reveal, or to cover and protect, the graft as required. The sheath may be formed to various shapes and sizes and geometries, such as conical and cylindrical shapes, to accommodate grafts of various sizes, shapes and configurations. The sheath may be split longitudinally along a side of the sheath, so that it can be removed from the device, or positioned over the device, even when the graft is deployed. Alternatively, a cross section of the sheath may be C-shaped, or less than annular, to facilitate removal and replacement of the sheath.

When the graft is in the position shown in FIG. 9, and is ready to be secured, all elements of the device for delivery of the graft for attachment to tissue are present on an operator side of the graft, with the flexible fingers forming the radial array. Of necessity, a small portion of the connector(s) may be extend through the graft to the distal side of the graft; however, the elements of the device are on the proximal side, so that it is not necessary to form a hole or void in the graft for positioning a bolster or other support device.

Figure 10:
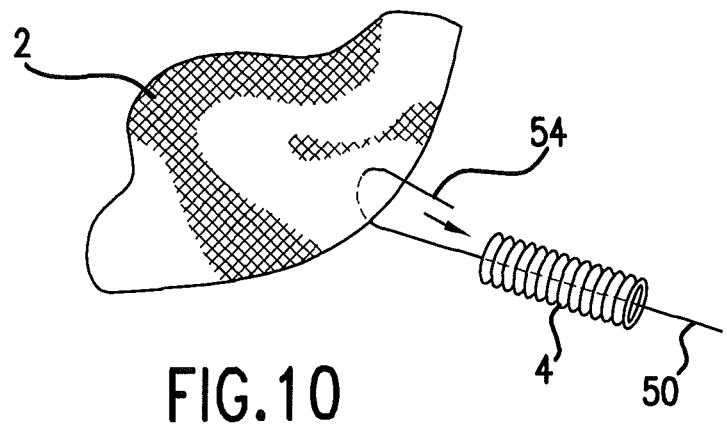
FIG. 10, FIG. 11 and FIG. 12 show progressive attachment of the graft attachment to tissue according to an embodiment of the device.
Figure 11:
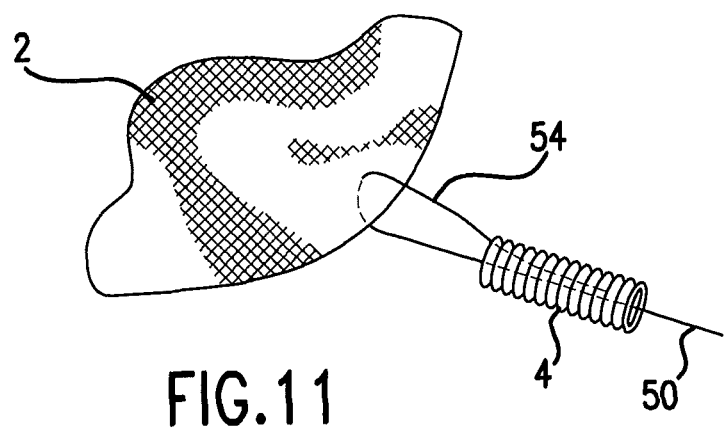
Figure 12:
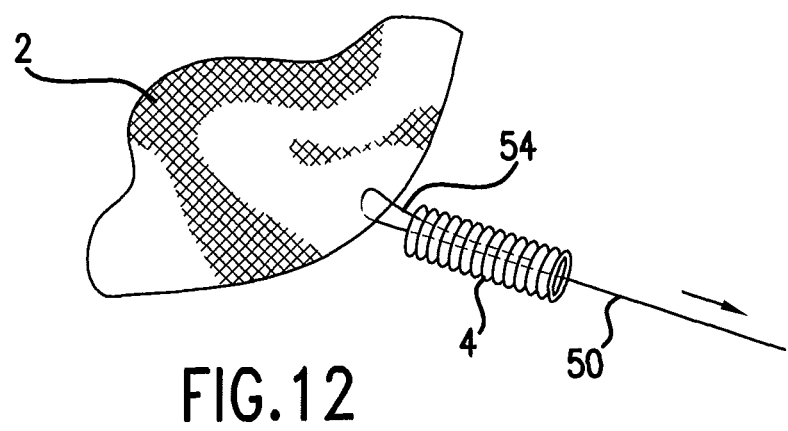
Figure 13:
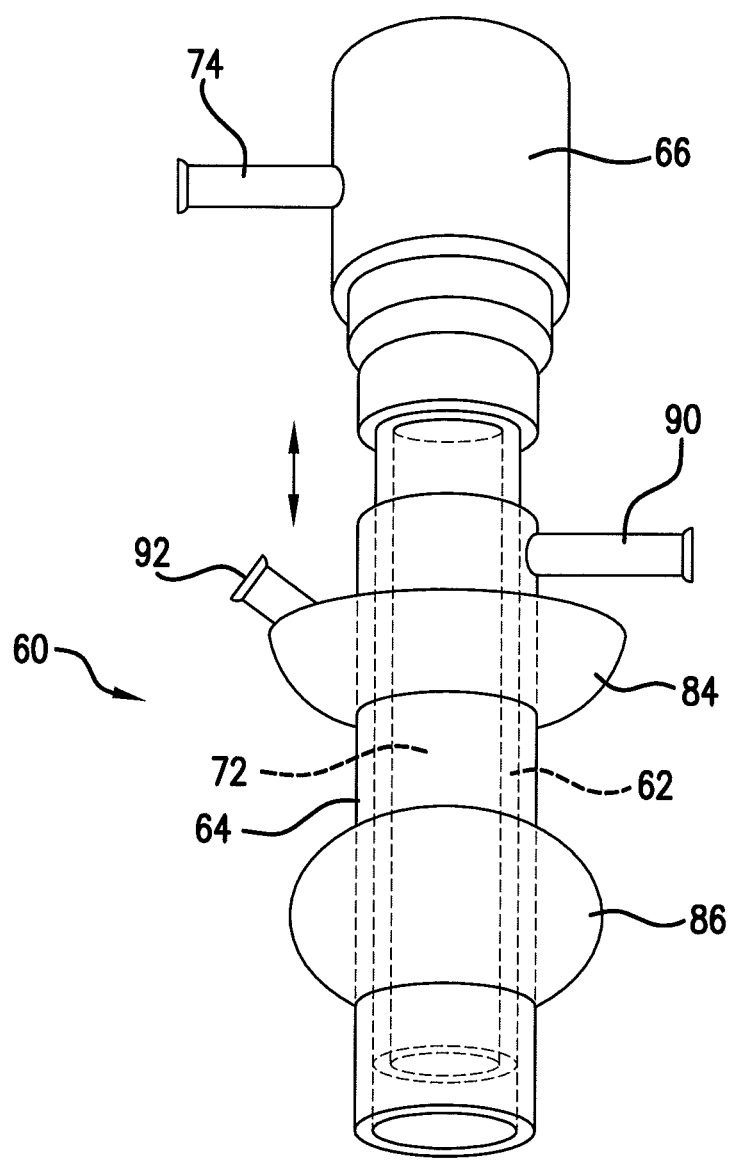
FIG. 13 is a perspective view of a novel trocar that is useful with the delivery device.
Figure 14A:
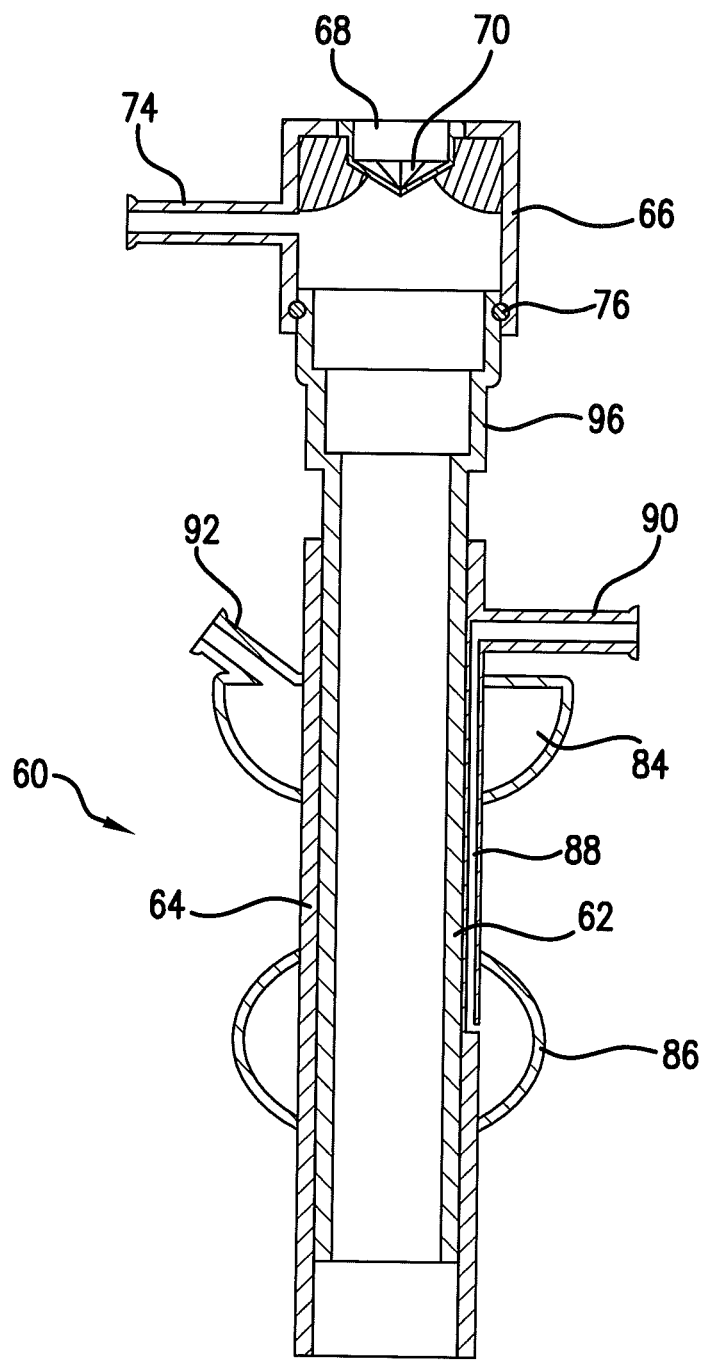
FIG. 14a is a sectioned view of the novel trocar.
Figure 14B:
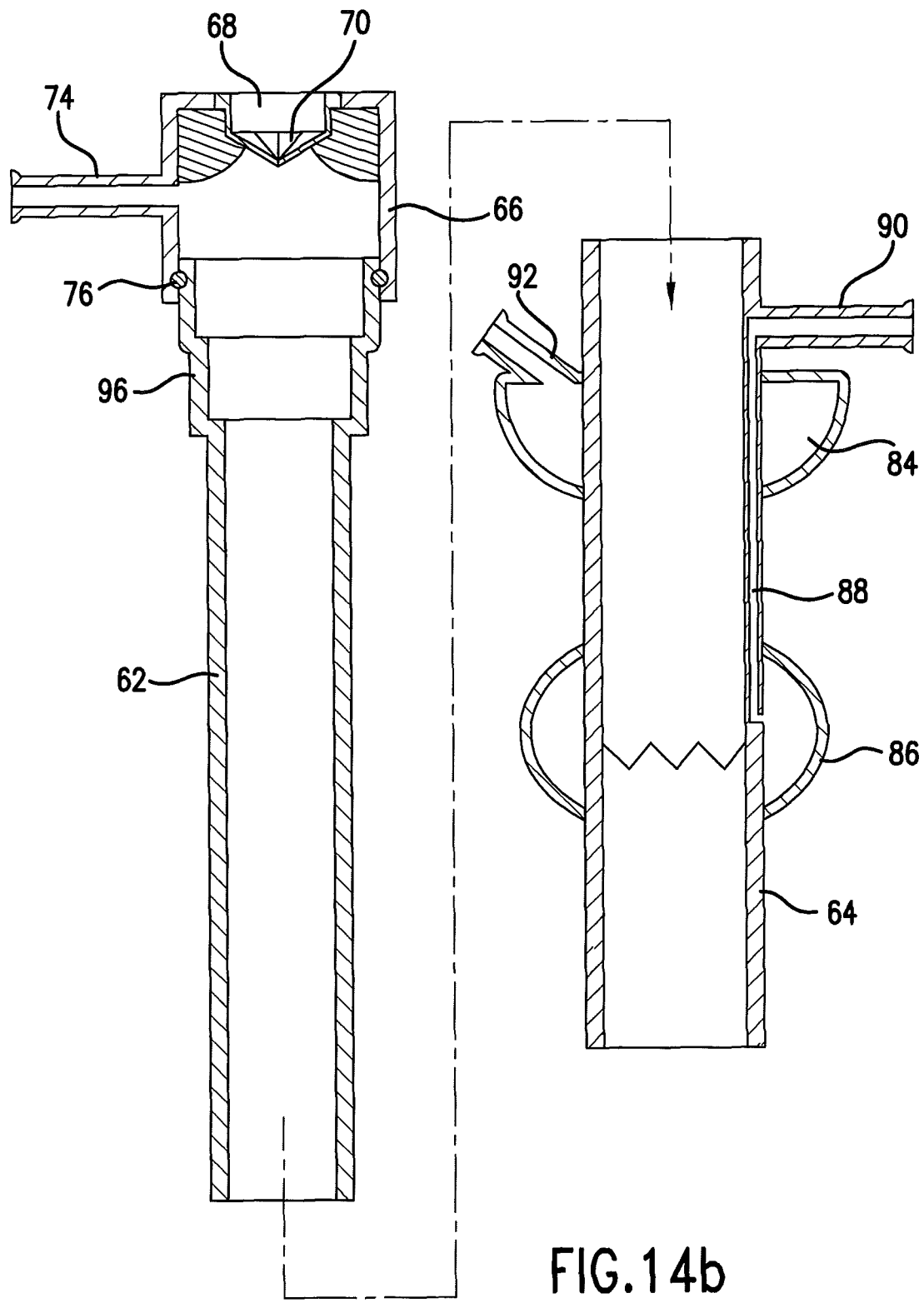
Figure 15:
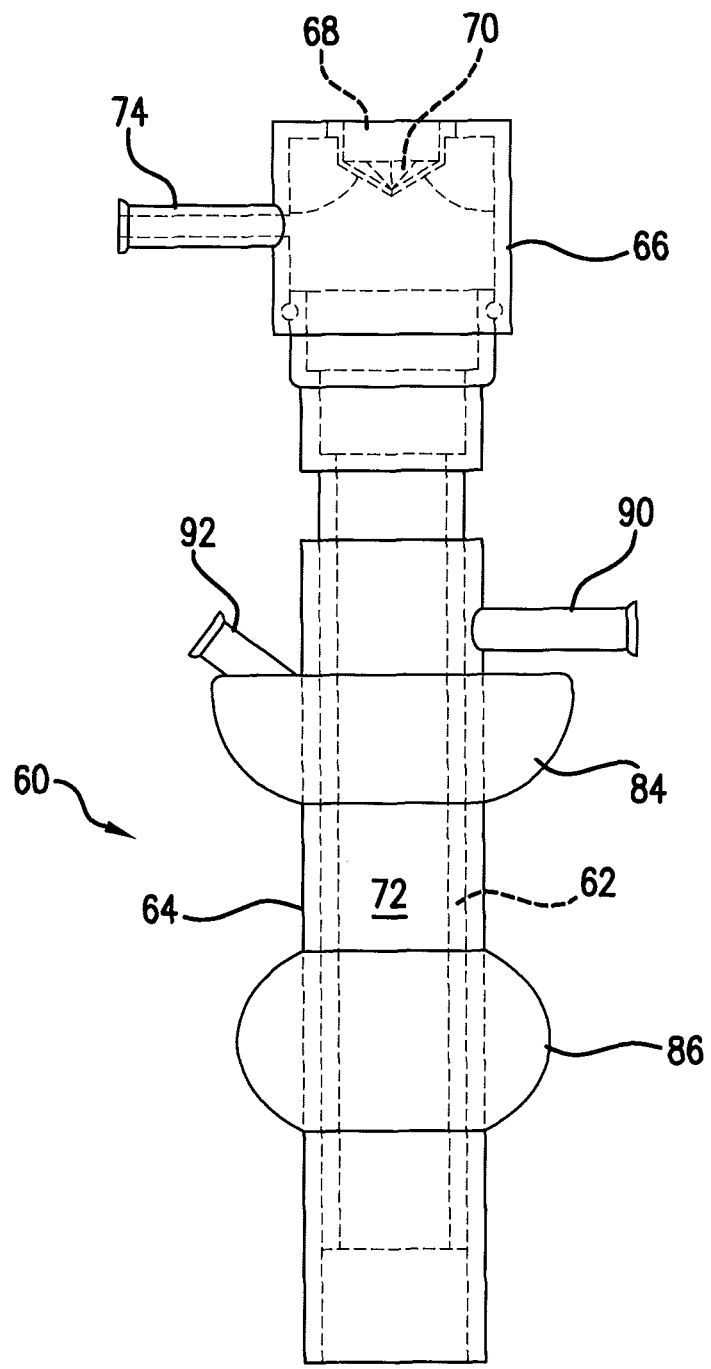
FIG. 15 is an elevation of the novel trocar.
Figure 16:
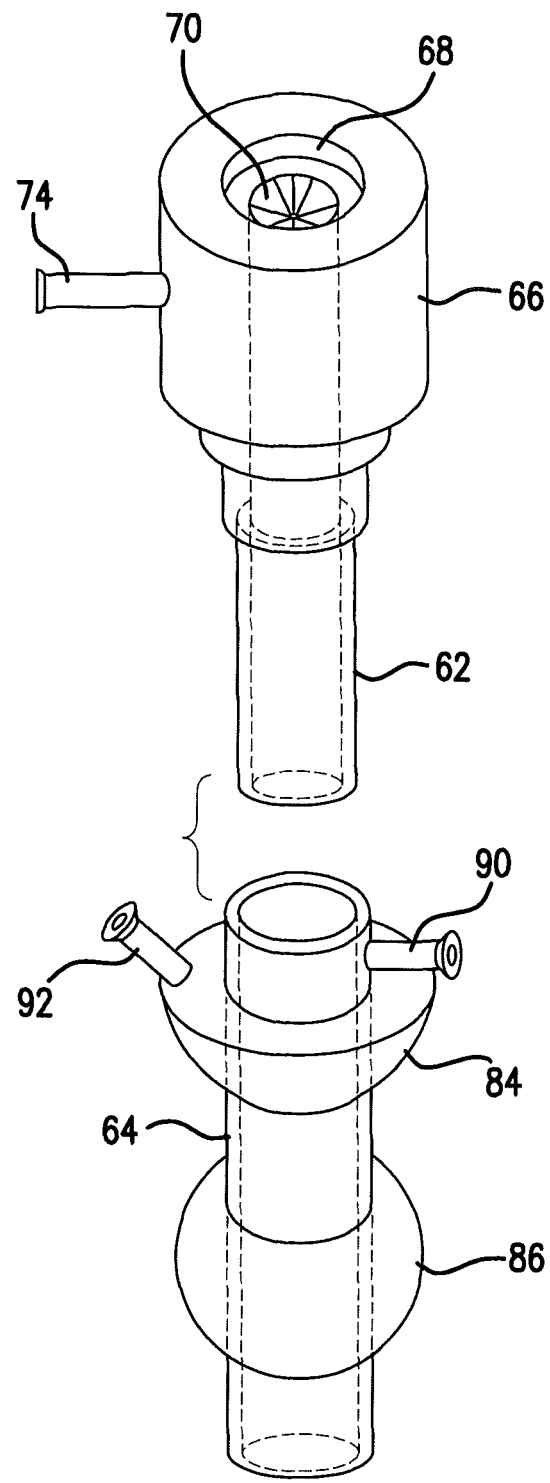
FIG. 16 is an exploded view of the novel trocar.

FIG. 10, FIG. 11 and FIG. 12 show another embodiment of the connector formed of wire. The connector 54 may be formed in a portion of a connector wire 50, such as a distal end of the wire, formed as a loop. The connector may be nitinol wire than has the loop imparted as shape memory, but is sufficiently deformable with low levels of force applied so as to allow the connector wire to be connected and disconnected from the graft. One connector is preferred to be associated with each flexible finger. The connector passes from the lumen of the hollow cable, through the graft, and back into the lumen of the cable. The wires 50 are connected at a proximal end to control rod 42 as described above. The connectors 54 are removed from the graft after the graft is installed, with control rod 42 used to pull the connectors through the graft to the proximal side of the graft. FIG. 12.

In use, according to one embodiment, a section of graft of appropriate size to repair the subject hernia is selected and/or formed. The graft may be formed (of various biological materials or, synthetic materials, including, but not limited to polypropylene or polytetrafluoroethylene (PTFE). The graft is connected near its perimeter to the connectors near the distal ends of the flexible fingers. Each flexible finger is preferred to have a connector. The actuator is moved to the position shown in FIG. 1, with the flexible fingers positioned generally parallel to the axis of travel of the actuator. This essentially folds the graft so that it is held as shown in shown in FIG. 2a, which is similar to a folded parachute configuration. The graft may also be positioned partly or wholly within the flexible fingers, as shown in FIG. 2b.

Figure 8:
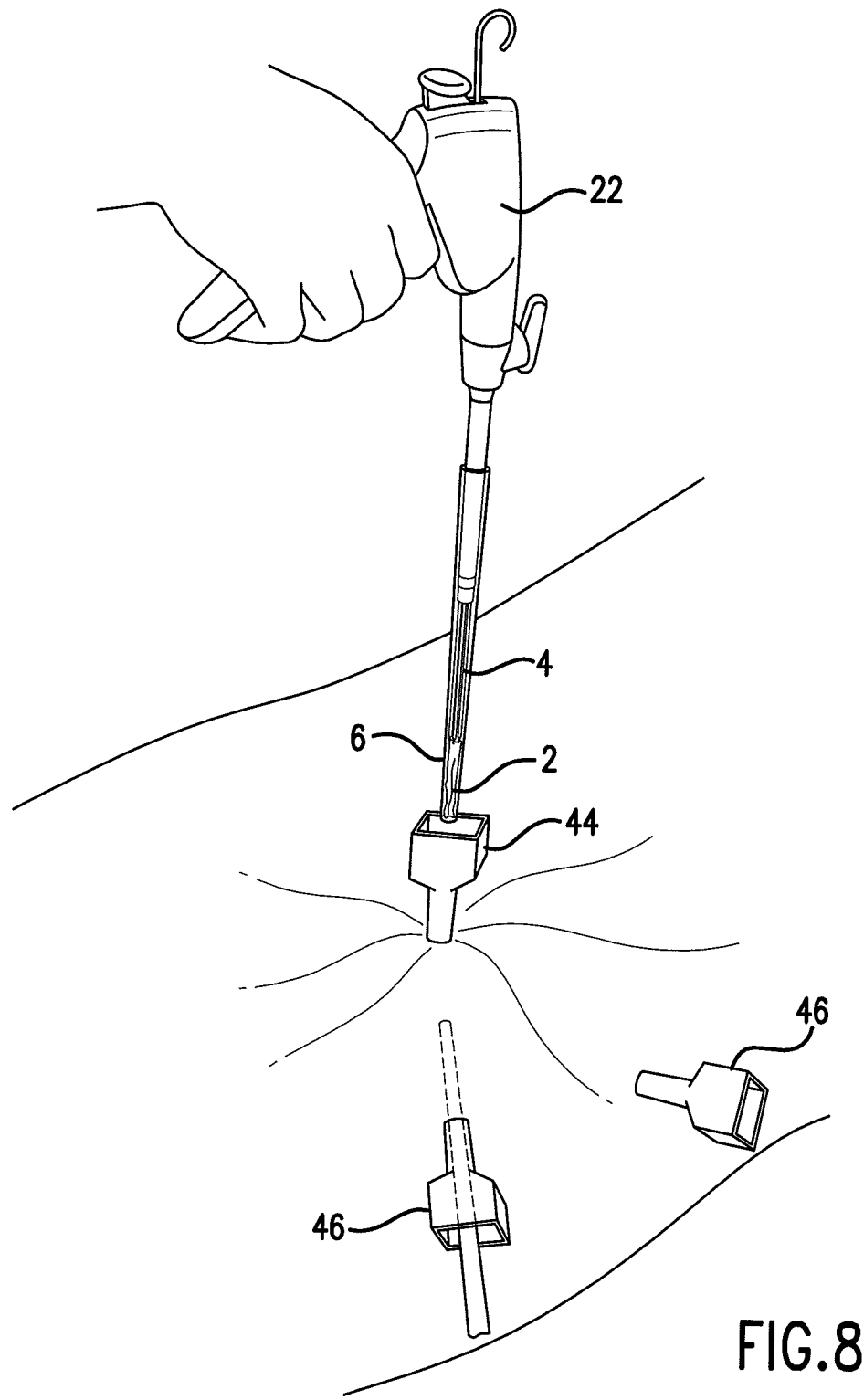
FIG. 8 demonstrates deployment of the graft for attachment to tissue through a trocar according to an embodiment of the device.
Figure 19:
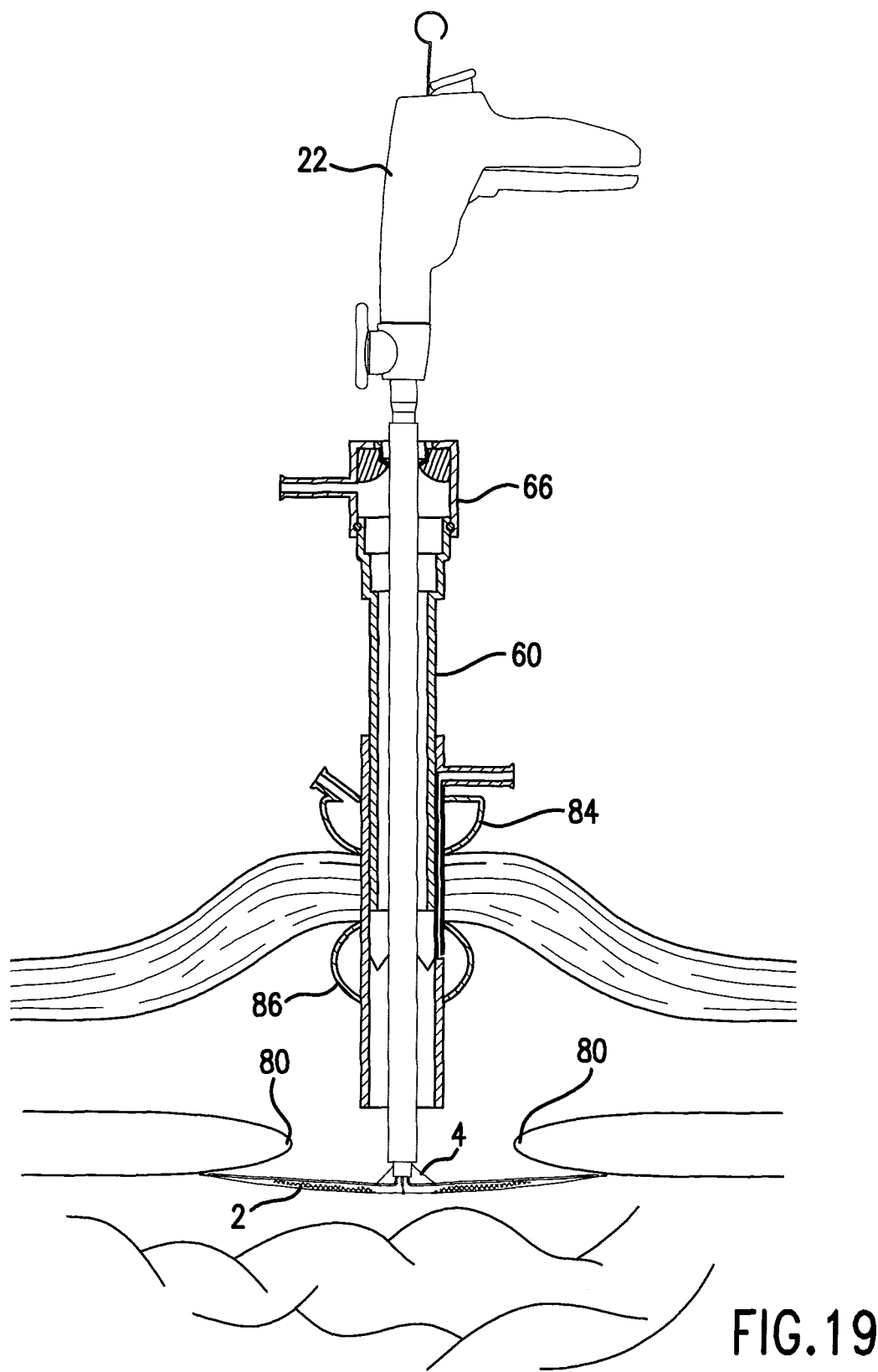
FIG. 19 is a sectioned view demonstrating use of the delivery device in situ in a ventral hernia.

An incision is made at the approximate center of the defect. FIG. 8. Trocar 44 or trocar 60 is inserted through the incision. The device is therefore inserted through the approximate center of the defect. FIG. 19. The trocar provides a port for entry of the device of the invention, and the device is inserted through the trocar. The sheath 6 covers the graft at this point in the process, retarding the graft from catching or snagging on the entry port, such as the trocar. The sheath may be slidable relative to the actuator. The locking mechanism holds the flexible fingers and the graft in this position.

After the distal end of the device is inserted through the incision and sufficient clearance is present, the sheath is pulled toward the operator, or is removed, and the trigger 16 of the device is moved from the position of FIG. 1 to the position of FIG. 3, causing the actuator to push the flexible fingers and associated graft to the position shown in FIG. 9 and FIG. 19. The graft is pulled up against the tissue, by means of the handle, to cover the hernia defect. The graft is secured using a device 48 as determined by the surgeon, and near the perimeter of the graft area. As shown in FIG. 9, graft attachment may be provided by known methods of attachment of grafts. The procedure may be monitored by use of a laparoscope for proper positioning, and securing, of the graft.

The graft is formed to generally a planar form when the flexible fingers form the radial array. As noted, the fingers may move through an arc that is more than 90°. Therefore, the surface of the graft may be somewhat curved or non-planar, so that the edges or periphery of the graft is pushed against the tissue 80 and secured to the tissue to cover the defect. However, the mesh is still considered to be in a generally planar position as shown in FIG. 4, FIG. 9 and FIG. 19.

After the connectors are released from the graft, the locking control button rotates the locking lug from engagement with the actuator, and the trigger is used to pull the actuator toward the handle, causing the flexible fingers to return to the position shown in FIG. 2. The device may now be removed by pulling it out of the trocar.

The flexible fingers, by being flexible along their length, with no preformed angles, kinks or similar geometry, are sufficiently flexible to follow a path of retreat from the fully extended position of FIG. 4 to the position shown in FIG. 2, without disrupting the sutured graft, while also being sufficiently rigid to support the graft for positioning and securement at the defect site. If the flexible fingers were rigid, or contained preformed angles, the path of retreat would be dictated by such structure, and would prevent orderly and non-disruptive withdrawal of the device and the trocar from the surgical site.

FIGS. 13 through 16 depict a unique and novel trocar 60 that is useful with the delivery device and method described herein. The trocar is also useful in other medical procedures in which trocars are used.

In one embodiment, the trocar comprises an inner sleeve 62 and an outer sleeve 64. In the embodiment as shown, the inner sleeve forms an upper portion of the trocar, while the outer sleeve forms a lower portion of the trocar. The inner sleeve is slidably adjustable, or telescoping, relative to the outer sleeve. The overall height of the trocar may be adjusted as preferred or required by way of the slidable, telescoping feature. A frictional fit between the inner sleeve and the outer sleeve according to one embodiment allows the inner sleeve to move up or down relative to the outer sleeve. However, the inner sleeve remains in position relative to the outer sleeve, due to the frictional fit between the inner sleeve and the outer sleeve.

The inner sleeve may comprise a head 66 that is fixed to a neck of the inner sleeve. In the embodiment as shown, the head has an opening 68 in the top portion thereof that allows vertical access to the inner lumen 72 of the trocar. The head may have a valve 70 therein. Medical devices, such as the delivery device described herein, may enter the lumen of the trocar 60 through the valve. The valve permits the device to pass through the valve, but the valve may be constructed to close around the periphery of the device in the event gas for insufflation is employed. Materials, such as gas for insufflations, or liquids, may pass through the valve and into the lumen, but the valve resists the material from back-flowing out of a body cavity and through the valve.

The head may also have one (1) or more ports 74, as preferred or required. The ports may be used for transferring devices, or more commonly, materials, such as gases or liquids, into the lumen of the trocar and subsequently, into a body cavity.

In a preferred embodiment, the head is removably attached to the trocar 60. An O-ring 76 may be used to seal the mating surfaces of the head to the inner sleeve of the trocar.

The lower sleeve may comprise an upper bolster in an embodiment of the trocar 60. The upper bolster 84 may be formed of a resilient material. The upper bolster limits travel of the trocar into the body cavity, and rests against the skin of the patient to help hold the trocar in position. The upper bolster may be formed to a permanent form, or the upper bolster may be formed of an inflatable material, and be collapsible so that the upper bolster does not interfere with further travel of the trocar 60 into a body cavity. If the bolster is inflatable, an access port 92 for inflation of the upper bolster may be provided.

The outer sleeve is also preferred to comprise an inflatable stabilizing member, or balloon 86. The inflatable stabilizing balloon is collapsible, so that travel of the trocar through layers of skin, muscle, or other tissue is not materially inhibited by the balloon.

The balloon is inflatable after the trocar is in position. A conduit 88 provides communication between the balloon and a port 90 that extends from the outer sleeve, as shown in the preferred embodiment of the drawing figures. Pressurized gas, such as nitrogen, may be used to inflate the balloon to a pressure that expands the balloon, by connecting a gas source to the port. The gas is transported through the conduit and into the balloon to inflate the balloon. In another embodiment, an air filled syringe may be used to inflate the balloon.

The inner sleeve may be sloped or stepped 96 at an upper portion thereof to allow a relatively large opening, while also providing a funnel. The relatively larger opening also allows a head of sufficient size to be attached to the device.

Figure 17:
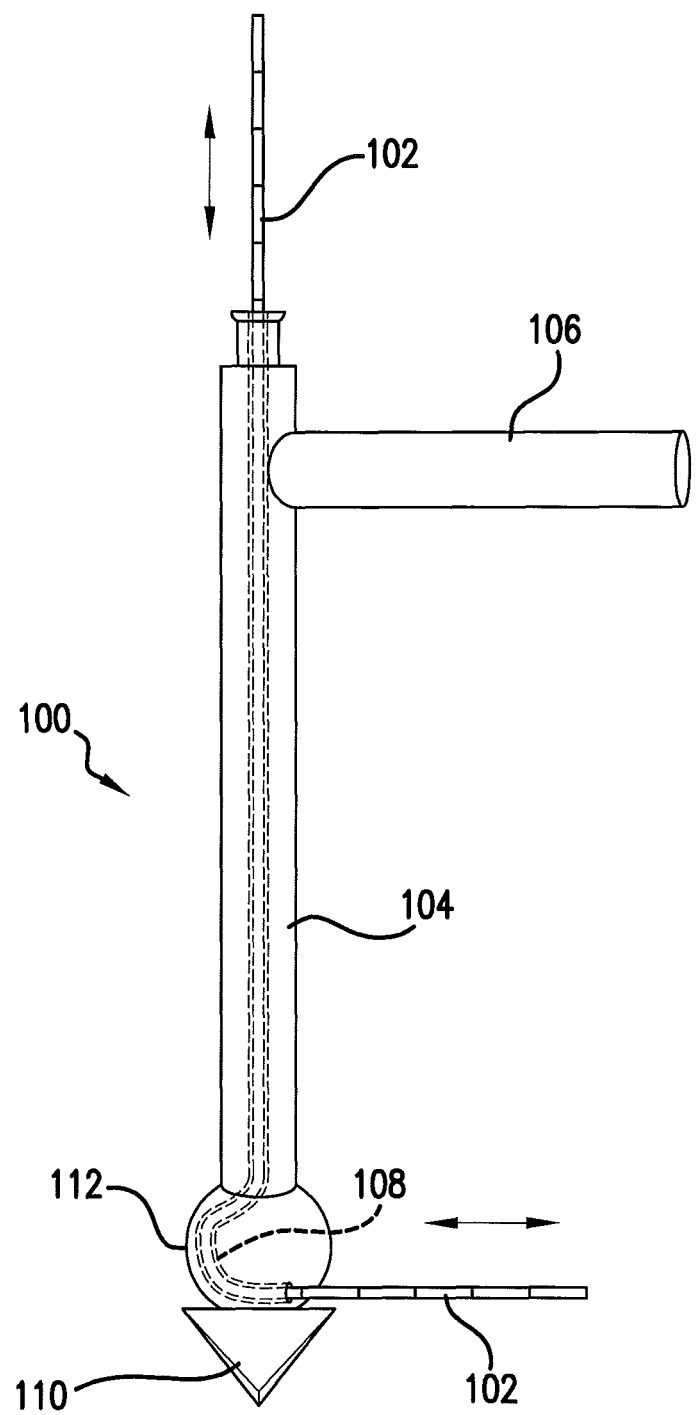
FIG. 17 is an elevation of the measuring device.
Figure 18:
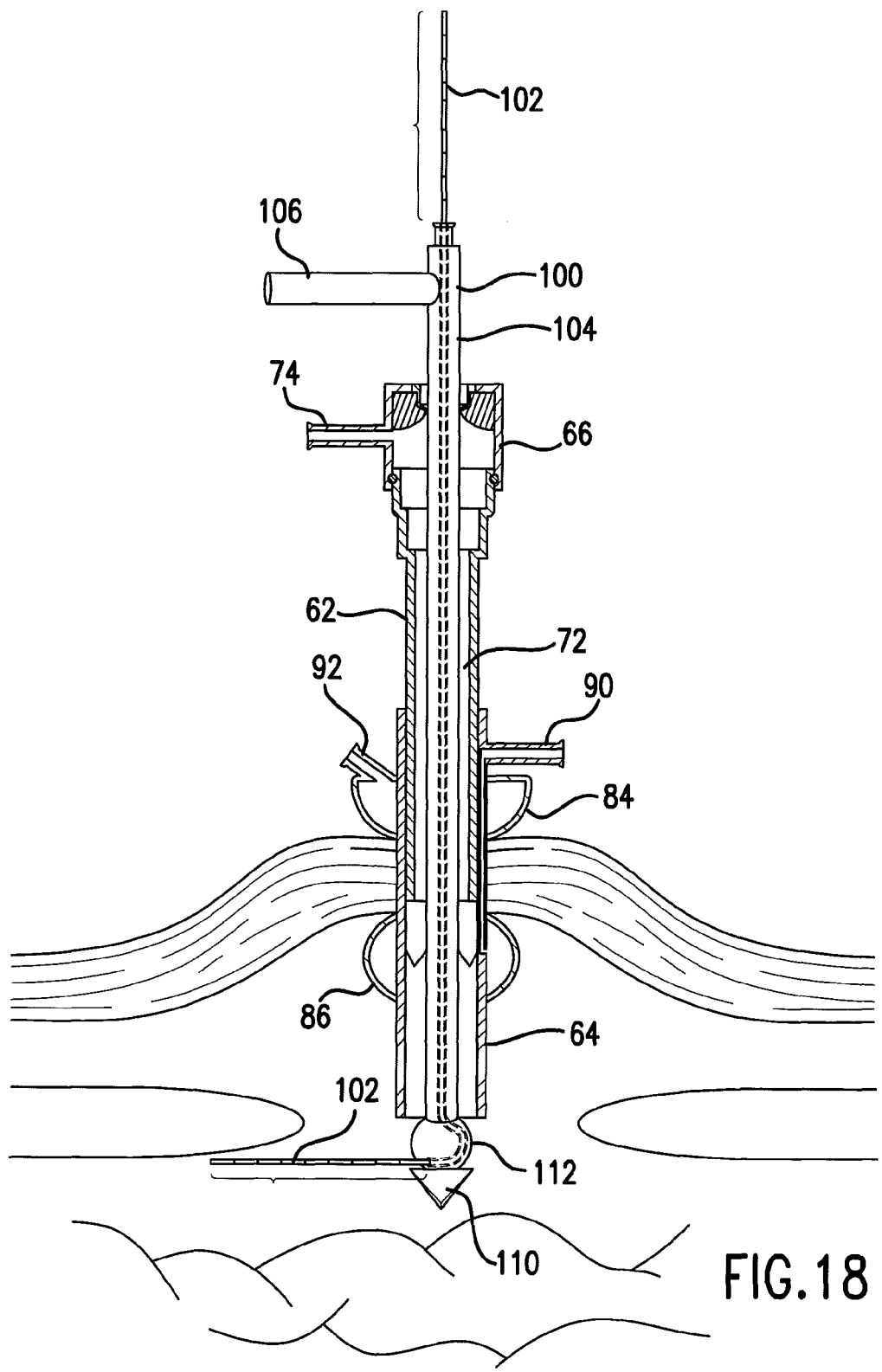
FIG. 18 is a sectioned view demonstrating use of the novel trocar and measuring device in situ in a ventral hernia.

In use, according to the embodiment as shown, the balloon 86 is deflated. The inner and outer sleeves are positioned as desired relative to each other through the slidable, telescoping feature of the device. The outer sleeve is pushed into the body cavity until the bolster rests against the skin of the patient. The stabilizing balloon is inflated, with the stabilizing balloon inside the body cavity and the bolster positioned outside the body cavity. The bolster and the balloon are spaced apart so that skin, muscle and other tissue is positioned between the bolster and the balloon as shown in FIG. 18. The bolster may be inflated through the access port if required. The trocar is now in position for use with a medical device, such as the delivery device described above, and/or the measuring device as described herein, or with other devices, or as a transport conduit for materials, including liquids and gasses FIGS. 17 and 18 show a measuring device 100 that is useful with the delivery device described herein. The measuring device may be utilized by placement through the trocar 60 as described herein. The measuring device may be used with some trocars previously known and used.

As shown in FIG. 17, the measuring device comprises a scale 102 and a trocar 104. The trocar 104 has a central lumen running generally through the central axis of the trocar 104. The trocar 104 may be delivered through the trocar 60 depicted in FIGS. 13-16 and described herein. The trocar 104 may have a handle 106 for positioning the trocar. The measuring scale is formed in an elongated structure. The elongated structure presents indicia at defined intervals. For example, the indicia may be a series of marks at equally spaced intervals, such as 1 cm. Alternatively, color bands of a particular, and defined width, such as 1 cm, may be provided. The color bands may be individually color coded. The indicia, such as the color bands, are viewable with a laparoscope.

The measuring scale is preferred to be formed of shape memory material. The shape memory material permits the measuring scale 102 to be transitioned from a generally vertical position to a generally horizontal position as shown in FIG. 17. Bending of the measuring scale is achieved by the lumen of the trocar 104, which is generally vertical for most of the length of the trocar as shown in FIG. 17, but transitions, by means of a generally horizontal exit port in the trocar, through use of an arcuate bend or an elbow 108 in the lumen. The bend or elbow may be angled to achieve a 90° turn of the measuring scale from the entrance to the trocar to the exit from the port of the trocar 104, but the turn could be any angle that is suitable for the particular surgical procedure, such as 80°, 100°, 110° or 120°, or other values within that range.

In one embodiment, a bulb 112 formed in a lower end of the trocar 104 allows the measuring scale to travel though a larger arc prior to exiting the port in the trocar 104. This prevents the measuring scale from making a hard, substantially right angle, turn and allows the device to travel smoothly and cleanly through the lumen.

A blade 110 may be formed in a lower end of the trocar 104. The blade allows the surgeon or other operator to pierce tissue to introduce the trocar into the body. The scale does not extend from the trocar during the process of piercing tissue.

In a preferred embodiment, the measuring device is used to measure the appropriate size for the graft or synthetic mesh. The trocar is positioned and stabilized as shown in FIG. 18, through use of the bolster 84 and the balloon 86. The measuring device is then inserted into the trocar 60, so that a lower end of the trocar 104 is substantially even with the defect. The measuring scale 102 is retracted into its trocar during the delivery of the trocar 104 through the trocar 60.

After the trocar 60 is in position as shown in FIG. 18, the measuring scale is pushed from above until it extends out of the port of the trocar. The surgeon monitors the progress of the measuring scale, such as with a laparoscope. When the measuring scale is properly positioned relative to the defect, the operator reads the gauge markings or indicia at the upper end of the scale. By determining how far the measuring scale has advanced, and reading the markings or indicia that are exposed at the upper end of the trocar, the surgeon determines the proper radius or size of the graft or mesh that will be required for the repair procedure as described above. The measuring scale may be rotated relative to the trocar, up to 360°. The measuring scale may be rotated in a sweeping motion relative to the defect, so that measurements are taken at multiple points of the defect. After the surgeon determines a preferred size of mesh or graft to be deployed using the delivery device, the graft is attached as described herein to the delivery device and the repair procedure is performed using the delivery device as described above.

The measuring device is useful in other applications where measurements internal to the body, such as a body cavity, are desirable.

What is claimed is:

1. A device for delivery of a graft for attachment to tissue, comprising:
    a plurality of spaced apart, flexible fingers;
    a plurality of control wires, wherein each of the control wires is connected to one of the flexible fingers at a distal end of the control wires;
    an actuator, wherein the actuator is movable outwardly relative to a handle, and the plurality of flexible fingers are in communication with, and move in response to movement of the actuator;
    wherein, proximal ends of the control wires are in a fixed position relative to movement of the flexible fingers as the flexible fingers and the actuator move outwardly relative to the handle, causing the control wires to exert a force on the flexible fingers and pull the flexible fingers as deployed by the actuator into a radial array.

2. A device for delivery of a graft for attachment to tissue as described in claim 1, wherein the plurality of flexible fingers travel through a range of motion of more than 90 degrees from an axis of travel of the actuator to form the radial array.

3. A device for delivery of a graft for attachment to tissue as described in claim 1, wherein the plurality of flexible fingers are formed of flexible cable.

4. A device for delivery of a graft for attachment to tissue as described in claim 1, wherein the plurality of flexible fingers are formed of flexible cable, and the flexible cable is hollow, coiled cable.

5. A device for delivery of a graft for attachment to tissue as described in claim 1, wherein a connector of the plurality of flexible fingers is constructed and arranged to connect to a graft.

6. A device for delivery of a graft for attachment to tissue as described in claim 1, further comprising a graft for attachment to tissue and a plurality of connectors, with one connector of the plurality of connectors positioned near a distal end of each of the flexible fingers, wherein the connectors are constructed and arranged to connect to the graft.

7. A device for delivery of a graft for attachment to tissue as described in claim 1, further comprising a graft, wherein all elements of the device for delivery of the graft for attachment to tissue are present on an operator side of the graft when the flexible fingers form the radial array.

8. A device for delivery of a graft for attachment to tissue as described in claim 1, further comprising a graft, wherein the graft is arranged to a generally planar form when the flexible fingers form the radial array.

9. A device for delivery of a graft for attachment to tissue as described in claim 1, wherein the actuator is movable toward the handle, and as the actuator moves toward the handle, the plurality of flexible fingers moves from the radial array and upwardly towards the axis of travel of the actuator as the actuator moves toward the handle.

10. A device for delivery of a graft for attachment to tissue as described in claim 1, further comprising a sheath that covers the plurality of flexible fingers, and the plurality of flexible fingers exit at a distal end of the sheath when the plurality of flexible fingers are moved outwardly from the handle to form the radial array.

11. A device for delivery of a graft for attachment to tissue as described in claim 1, further comprising a sheath, wherein the actuator is movable toward the handle to move the plurality of flexible fingers to a position that is generally parallel to an axis of travel of the actuator, wherein the plurality of flexible fingers is positioned within the sheath when the actuator is fully moved toward the handle.

12. A device for delivery of a graft for attachment to tissue as described in claim 1, further comprising a sheath, wherein the sheath is advanced away from and retracted toward the handle, and wherein the sheath covers the flexible fingers when the sheath advances away from the handle and the sheath reveals the flexible fingers when the sheath is retracted toward the handle.

13. A device for delivery of a graft for attachment to tissue as described in claim 1, further comprising a sheath, wherein the sheath is advanced away from and retracted toward the handle, and wherein the sheath covers a graft that is connected to the flexible fingers when the sheath advances away from the handle and the sheath reveals the graft when the sheath is retracted toward the handle.

14. A device for delivery of a graft for attachment to tissue as described in claim 1, further comprising a sheath, wherein the sheath is advanced away from and retracted toward the handle, and wherein the sheath folds a graft that is connected to the flexible fingers within the sheath when the sheath advances away from the handle, and the sheath reveals the graft when the sheath is retracted toward the handle.

15. A device for delivery of a graft for attachment to tissue as described in claim 1, wherein a graft is connected to the device by a plurality of wires that extend from the plurality of flexible fingers.

16. A device for delivery of a graft for attachment to tissue as described in claim 1, wherein a graft is connected to the device by a plurality of wires that extend from the plurality of flexible fingers, wherein the wires are formed of shape memory material.

17. A device for delivery of a graft for attachment to tissue as described in claim 1, further comprising a trocar, wherein the trocar comprises an outer sleeve and an inner sleeve, wherein the outer sleeve is positioned over, and is slidable relative to the inner sleeve, and wherein a lumen extends through both the outer sleeve and the inner sleeve, wherein the lumen opens at a top and a bottom of a construct formed by the outer sleeve and the inner sleeve, and the lumen extending through the outer sleeve communicates with the lumen extending through the inner sleeve.

18. A device for delivery of a graft for attachment to tissue as described in claim 1, further comprising a trocar, wherein the trocar comprises a lumen extending from an upper portion to a lower portion thereof and further comprising a measuring scale, said measuring scale having measurement indicia thereon, said measuring scale extending through said lumen and out of a lower portion of the lumen, wherein the measuring scale is formed of shape memory material, and a length of the measuring scale is deformed by the trocar as the measuring scale traverses the trocar, and the measuring scale assumes a generally straight configuration upon exit from the lower portion of the lumen of the trocar.

19. A device for delivery of a graft for attachment to tissue as described in claim 1, further comprising a trocar, wherein the trocar comprises a lumen extending from an upper portion to a lower portion thereof and further comprising a measuring scale, the measuring scale having measurement indicia thereon, said measuring scale extending through the lumen and out of a lower portion of the lumen, wherein an angle of exit of the measuring scale from the lumen is 80° to 120° wherein the measuring scale is formed of shape memory material, and a length of the measuring scale is deformed by the trocar as the measuring scale traverses the trocar, and the measuring scale assumes a generally straight configuration upon exit from the lower portion of the lumen of the trocar.

20. A device for delivery of a graft for attachment to tissue as described in claim 1, further comprising a trocar, wherein the trocar comprises a lumen extending from an upper portion to a lower portion thereof and further comprising a measuring scale, the measuring scale having measurement indicia thereon, said measuring scale extending through the lumen and out of an upper portion of the lumen and out of a lower portion of the lumen, wherein an angle of exit of the measuring scale from the lumen is 80° to 120° from an angle of entry of the measuring scale into the lumen, and wherein the measuring scale is formed of shape memory material and, wherein the measuring scale is formed of shape memory material, and a length of the measuring scale is deformed by the trocar as the measuring scale traverses the trocar, and the measuring scale assumes a generally straight configuration upon exit from the lower portion of the lumen of the trocar, and the measuring scale is positioned at an angle of 80° to 120° from the angle of entry of the measuring scale into the lumen.

21. A device for delivery of a graft for attachment to tissue as described in claim 1, further comprising a first trocar, wherein the first trocar comprises an outer sleeve and an inner sleeve, wherein the outer sleeve is positioned over, and is slidable relative to the inner sleeve, and wherein a lumen extends through both the outer sleeve and the inner sleeve, wherein the lumen opens at a top and a bottom of a construct formed by the outer sleeve, and the lumen extending through the outer sleeve communicates with the lumen extending through the inner sleeve, and the inner sleeve further comprising a second trocar that is present in the lumen of the first trocar, wherein the second trocar comprises a lumen extending from an upper portion to a lower portion thereof and further comprising a measuring scale, said measuring scale having measurement indicia thereon, said measuring scale extending through said lumen and out of a lower portion of the lumen.

22. A device for delivery of a graft for attachment to tissue as described in claim 1, wherein the plurality of flexible fingers are mounted in a holder, and wherein the plurality of flexible fingers are rotatable relative to the holder.

23. A device for delivery of a graft for attachment to tissue as described in claim 1, wherein each of the plurality of flexible fingers is constructed to comprise a variable length.

24. A device for delivery of a graft for attachment to tissue as described in claim 1, wherein a proximal end of each of the control wires is mounted to an article that is associated with the handle and is stationary relative to the actuator.

25. A device for delivery of a graft for attachment to tissue as described in claim 1, wherein a proximal end of each of the control wires is mounted to the device and constructed and arranged so that the proximal end of each of the control wires does not move as the actuator moves.

26. A device for delivery of a graft for attachment to tissue as described in claim 1, wherein the distal end of a control wire is attached to a flexible finger at a point that is less than 25% of a distance along a length of the flexible finger, as measured from the joinder of a proximal end of the flexible fingers to the distal end of the flexible finger.

27. A device for delivery of a graft for attachment to tissue as described in claim 1, wherein an acute angle of 30° to 60° degrees is formed by the control wires relative to the flexible fingers when the actuator is fully advanced.

28. A device for delivery of a graft for attachment to tissue as described in claim 1, further comprising a trocar, wherein the trocar comprises a lumen extending from an upper portion to a lower portion thereof and further comprising a measuring scale, said measuring scale having measurement indicia thereon, said measuring scale extending through said lumen and out of a lower portion of the lumen, wherein the measuring scale is formed of shape memory material, and a length of the measuring scale is deformed to an arcuate shape by the trocar as the measuring scale traverses the trocar, and the measuring scale assumes a generally straight configuration upon exit from the lower portion of the lumen of the trocar.

* * * * *